(12) United States Patent
Wardlaw

(10) Patent No.: US 6,692,496 B1
(45) Date of Patent: Feb. 17, 2004

(54) FRACTURE TREATMENT

(75) Inventor: Douglas Wardlaw, Stonehaven (GB)

(73) Assignee: Grampian University Hospitals NHS Trust, Aberdeen (GB)

( * ) Notice: Subject to any disclaimer, the term of this patent is extended or adjusted under 35 U.S.C. 154(b) by 0 days.

(21) Appl. No.: 09/830,887

(22) PCT Filed: Nov. 2, 1999

(86) PCT No.: PCT/GB99/03601

§ 371 (c)(1),
(2), (4) Date: Jul. 6, 2001

(87) PCT Pub. No.: WO00/25681

PCT Pub. Date: May 11, 2000

(30) Foreign Application Priority Data

Nov. 2, 1998 (GB) .............................................. 9823974

(51) Int. Cl.[7] .............................................. A61B 17/17
(52) U.S. Cl. ....................................................... 606/64
(58) Field of Search ............................. 606/64, 62, 98

(56) References Cited

U.S. PATENT DOCUMENTS

| 4,475,545 A | * | 10/1984 | Ender | |
| 4,522,201 A | | 6/1985 | Tongue | |
| 5,248,313 A | * | 9/1993 | Greene et al. | 606/62 |
| 5,374,271 A | | 12/1994 | Hwang | |
| 5,429,640 A | * | 7/1995 | Shuler et al. | 606/64 |
| 5,472,444 A | * | 12/1995 | Huebner et al. | 606/64 |
| 5,665,086 A | * | 9/1997 | Itoman et al. | 606/64 |
| 5,766,174 A | * | 6/1998 | Perry | 606/62 |
| 5,779,705 A | * | 7/1998 | Matthews | 606/67 |

FOREIGN PATENT DOCUMENTS

| BE | 678 171 | 9/1966 |
| DE | 92 06 580 | 7/1982 |
| EP | DE 43 41 677 C1 | 7/1995 |
| WO | WO 92 01422 | 6/1992 |
| WO | WO 95/15728 | 6/1995 |

\* cited by examiner

Primary Examiner—Ralph A. Lewis
(74) Attorney, Agent, or Firm—Drinker Biddle & Reath LLP

(57) ABSTRACT

The invention provides apparatus for the treatment of a bone fracture (18'), comprising an elongate member (2) adapted for substantially axial insertion into the bone (18) such that it spans the fracture; where in one embodiment the elongate member being formed, adjacent one or both of its proximal and distal ends with fixture location means (9) adapted to receive a fixing device (27) inserted transversely of the elongate member (2) and passing through part at least of the bone to be treated; the position of the fixture location means (9) and the line of insertion of the fixing device (27) being defined by a jig (21) temporarily affixable to the proximal end of the elongate member; wherein a guide means (25) is adapted to pass through the fixture location and act as a guide for the desired location of the fixing device, said apparatus also providing drill means (25a and 26a), guidable by the guide means, and utilizable to form a bore communicating with the fixture location and adapted to accommodate the fixing device.

19 Claims, 9 Drawing Sheets

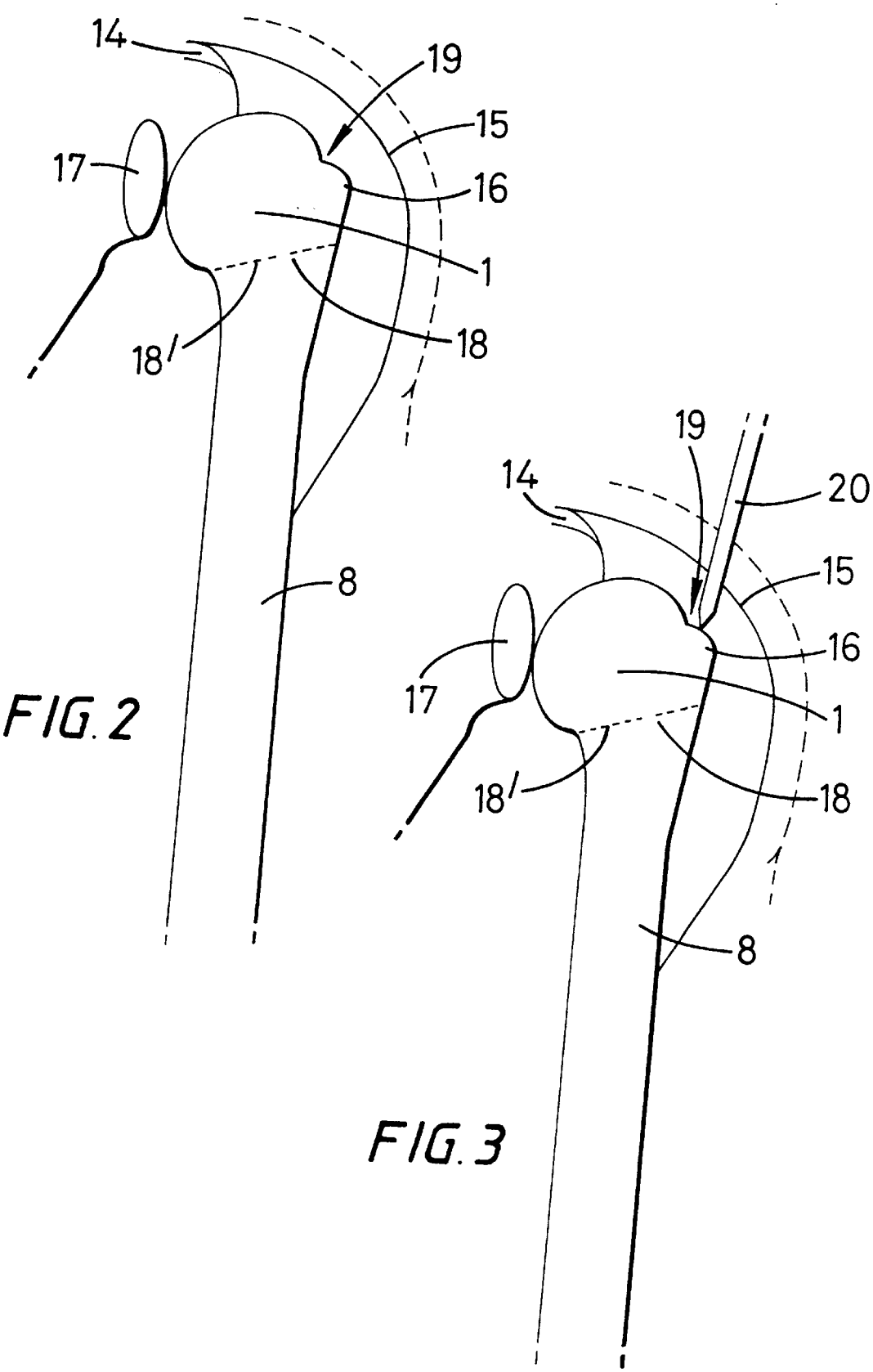

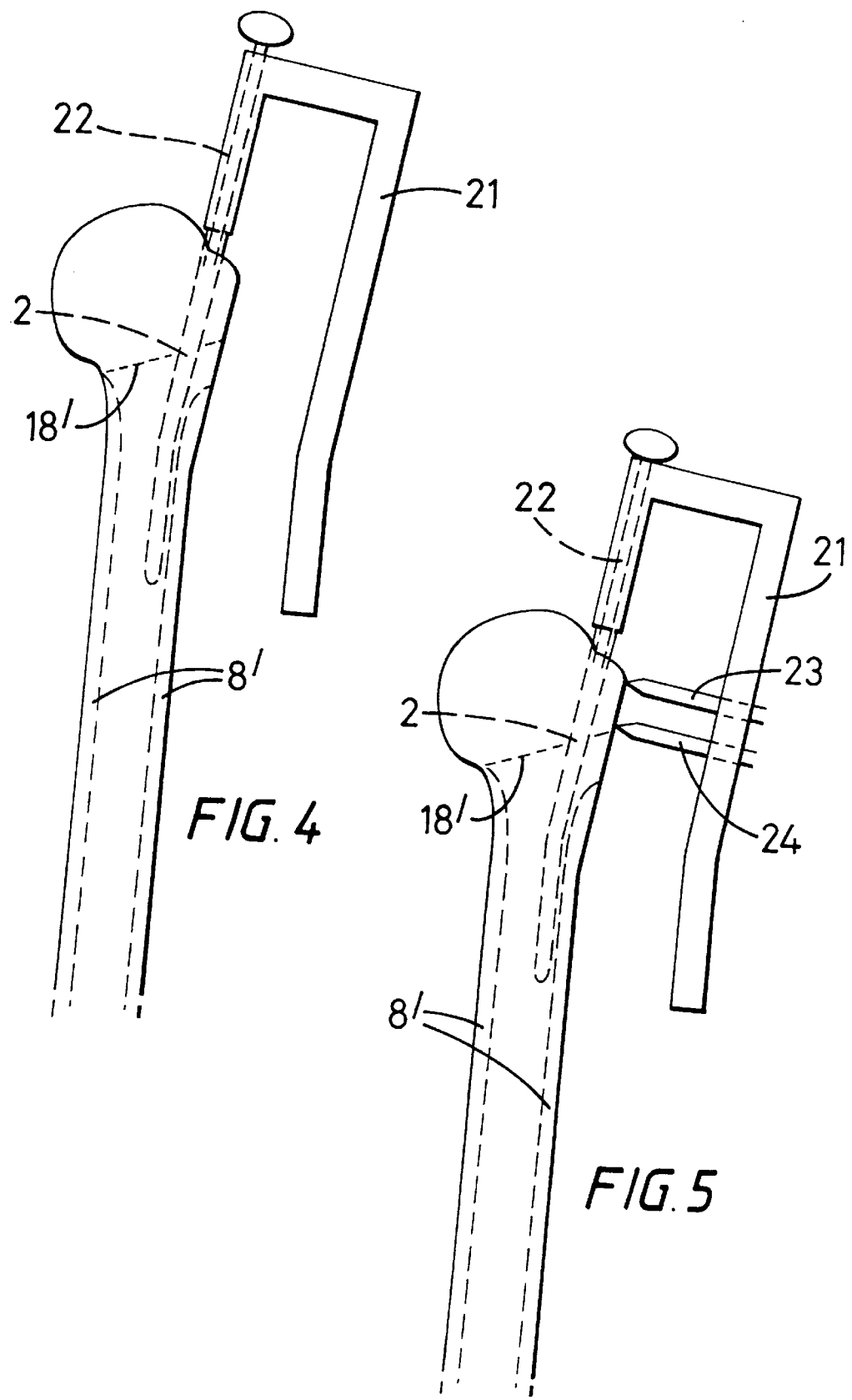

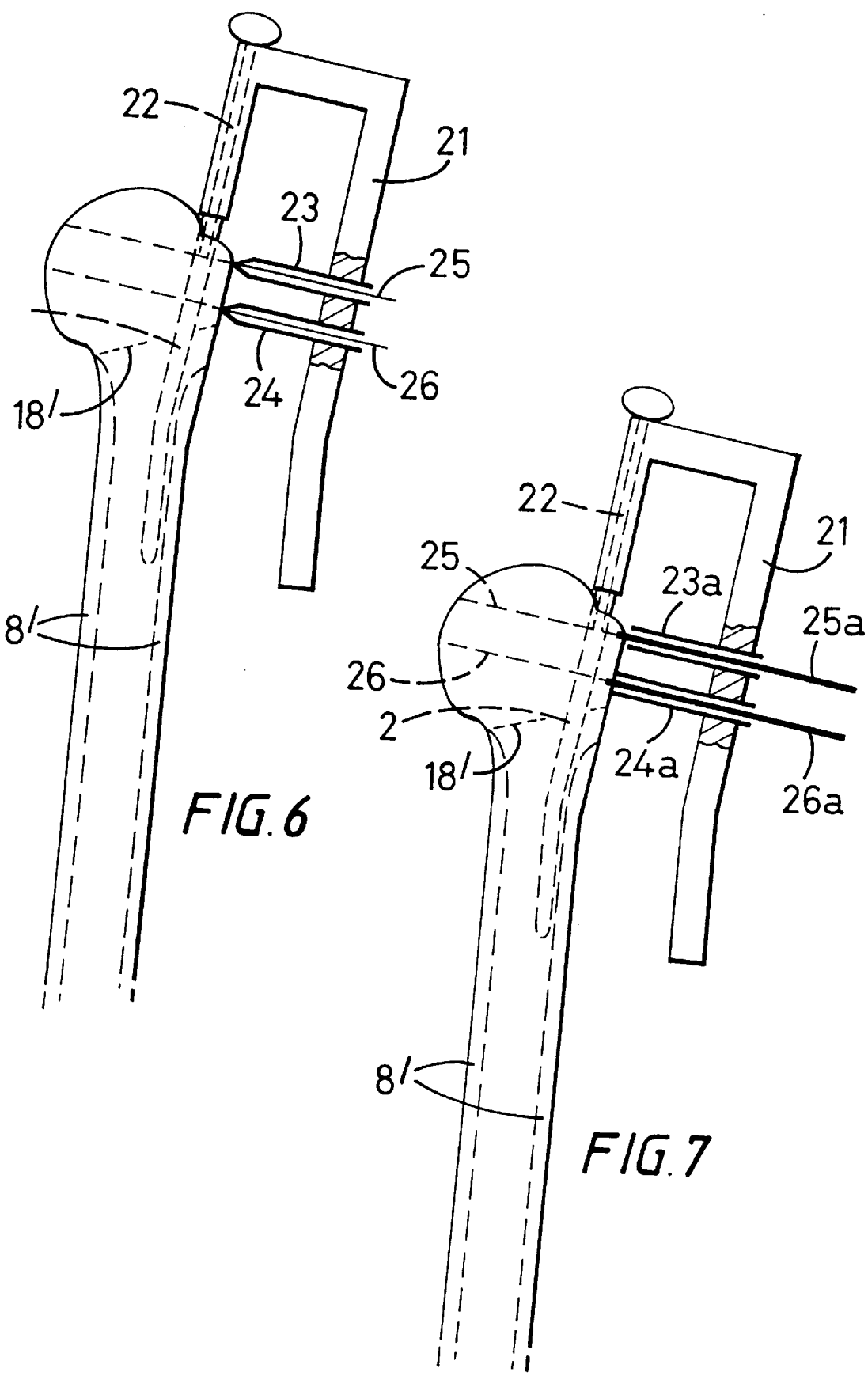

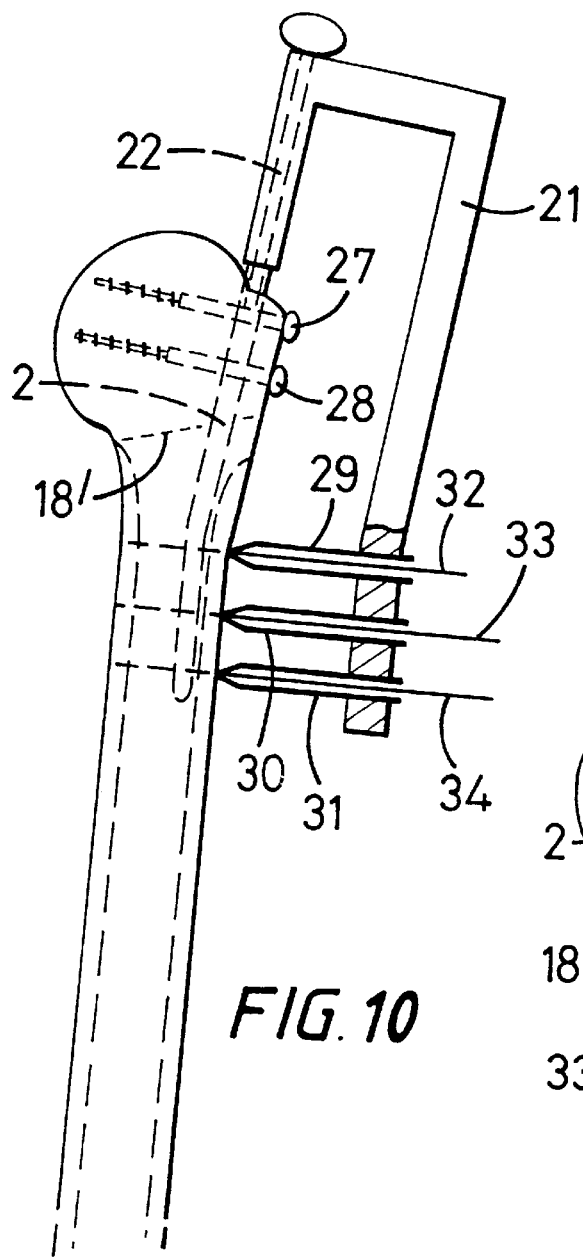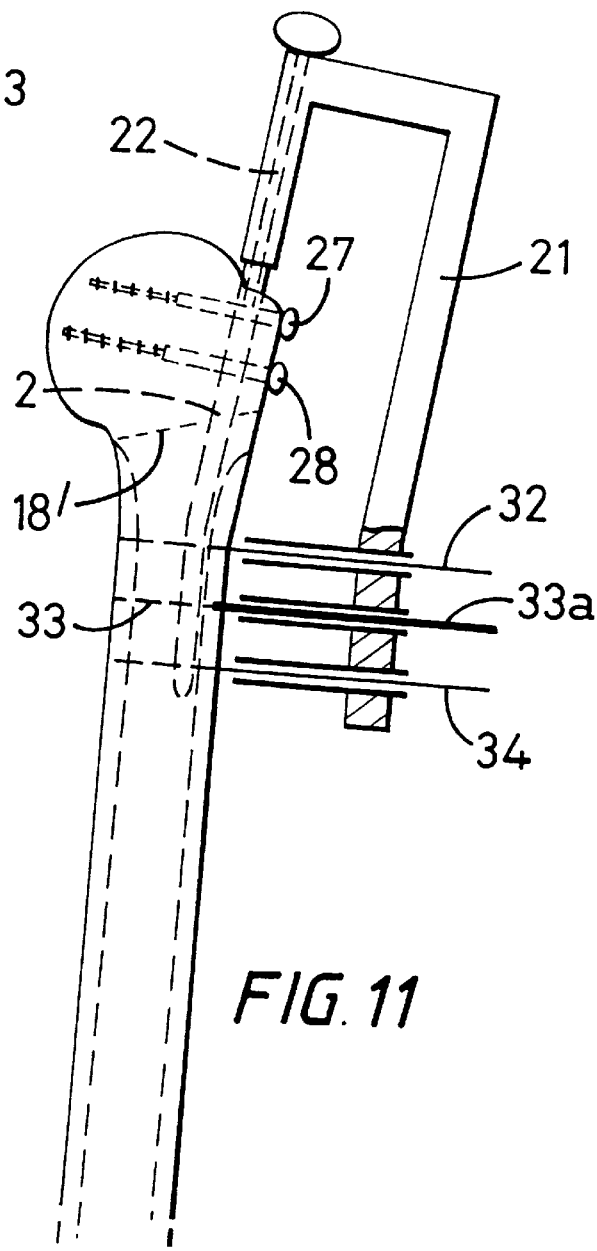
FIG. 10
FIG. 11

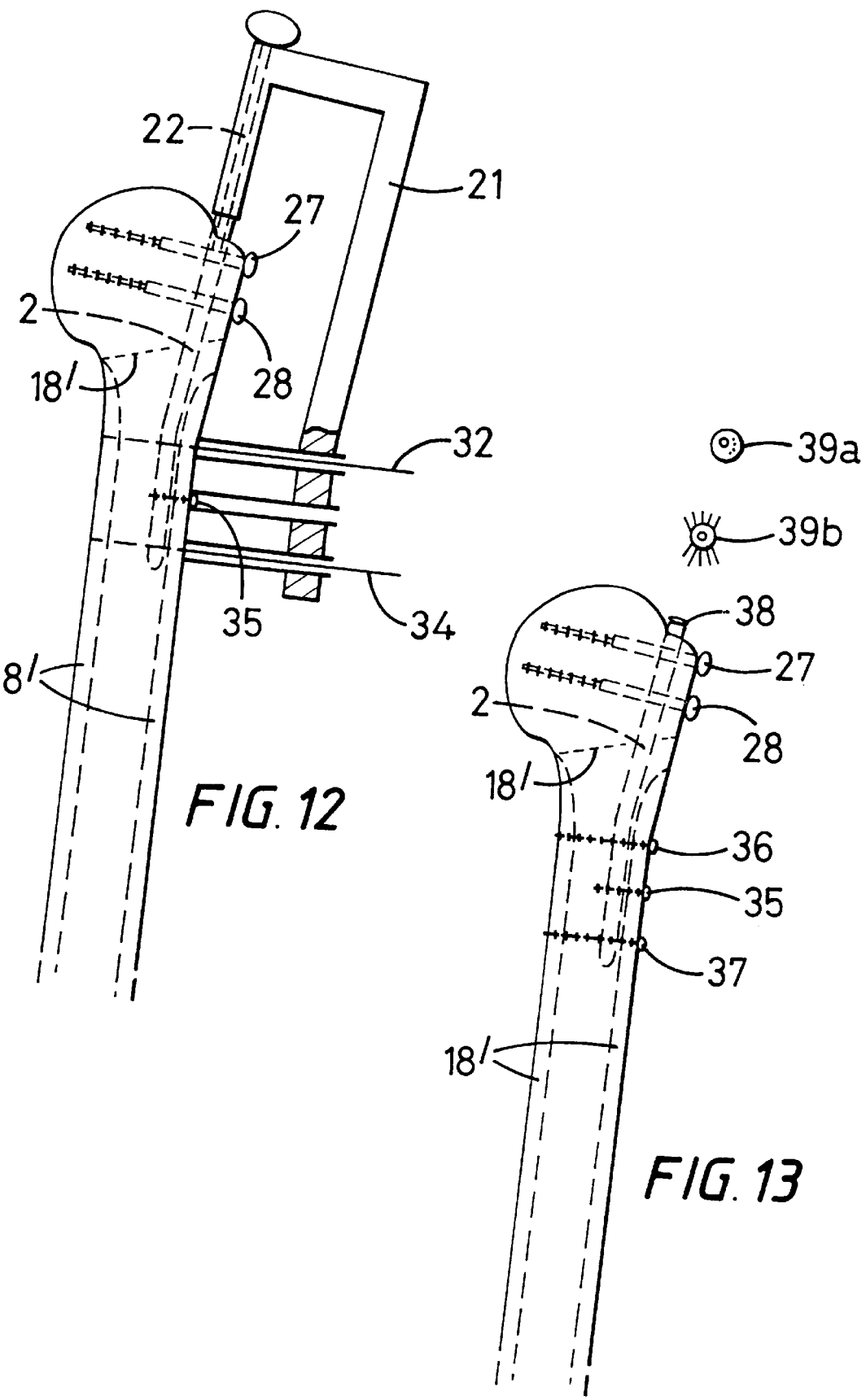

FRACTURE TREATMENT

FIELD OF THE INVENTION

This invention relates to the treatment of fractures, and it relates especially, though not exclusively, to apparatus for effecting such treatments as are applicable to fractures of long bones such as the humerus.

BACKGROUND OF THE INVENTION

A well established and highly successful procedure used in the treatment of long bone fractures involves the use of intramedullary nails which are inserted substantially axially of a bone and to one side of the fracture, and extend through the medullary cavity (reamed out if necessary) and past the region of fracture to an area of sound bone. The proximal end of such a nail is secured to the bone at or adjacent to the region of its entry into the bone, whereas the distal end of the nail has to be secured to the sound bone beyond the fracture. One difficulty associated with this procedure is the accurate location of the nail and its fixing points with which separate securing members, such as transversely inserted fixing devices, e.g. screws, need to engage.

It has previously been proposed to use radiographic techniques to assist the surgeon in this respect, but it is preferable to avoid subjecting a patient to radiation for such purposes, and accordingly various mechanical procedures have been developed in recent years. Such procedures typically involve the use of jigs which are attachable to the nail during the surgical alignment process and which provide predictive guidance as to the location of the nail (particularly the distal end thereof), thereby to ease the difficulty described above.

Alignment procedures of this general kind are described in GB 2 288 738 A; GB 2 258 154 A; WO 96/03085 A1; U.S. Pat. No. 5,352,228 and U.S. Pat. No. 4,913,137 and it is an object of this invention to provide improved apparatus and methods for the application, alignment and/or engagement of transverse fixing devices with intramedullary nails, and/or to effect improved stability and/or mobility of fractured bones.

SUMMARY OF THE INVENTION

According to the invention in one aspect there is provided an apparatus for the treatment of bone fracture, comprising an elongate member for substantially axial insertion into the bone such that it spans the fracture; the elongate member being formed, adjacent one or both of its proximal and distal ends with a fixture location means, which may comprise an aperture which is intended to receive a fixing device inserted transversely of the elongate member and passing through part at least of the bone to be treated; the position of the fixture location and the line of insertion of the fixing device being defined by a jig temporarily affixed to the proximal end of the elongate member; characterised in that a guide means is passed through the fixture location and acts as a guide for the desired location of the fixing device, and drill means guided by the guide means, is used to form a bore communicating with the fixture location, said bore being adapted to accommodate the fixing device.

Preferably the guide means comprises a wire, such as a K-wire, and the drill means is axially apertured to accommodate said wire.

According to another aspect of the invention there is provided an apparatus for the treatment of bone fracture, comprising an elongate member for substantially axial insertion into the bone such that it spans the fracture, the elongate member being formed, adjacent at least its distal end with a fixture location intended to receive a fixing device inserted transversely of the elongate member and to engage with an aperture present in the elongate member so as to permit the elongate member to be drawn into intimate contact with the inner surface of cortical bone, thereby to enable the elongate member to act as a support member.

Preferably the fixing device is a screw and the fixture location comprises an internally threaded aperture formed in said elongate member.

Preferably the elongate member is formed with a plurality of further apertures adjacent the distal end thereof, any or all of which further apertures may be internally threaded.

Preferably, the elongate member comprises an intramedullary nail configured in the region thereof occupied by said aperture and possibly also said further apertures to permit its close conformity to the inner cortical wall of said bone.

Preferably also the proximal end of said elongate member also is formed with one or more apertures to accommodate transversely disposed fixing devices.

Where a plurality of said fixing devices is employed to cooperate with respective apertures adjacent the proximal end of said elongate member, said fixing devices are adapted to pass through the elongate member and into sound bone and are deployed in substantially parallel planes transverse to said elongate member, but are misaligned so as to respectively engage areas of bone more widely separated than the areas that would have been engaged by the fixing devices had they been disposed in alignment with one another.

In an alternative embodiment, an elongate member is adapted to be passed through a fixing device whereafter the fixing location of the proximal end of said elongate member resides in contact with the fixing device.

Conveniently, the said fixing device may comprise an aperture whereby said elongate member can pass through the fixing device in use.

According to a further aspect of the invention there is provided a method for the treatment of bone fracture, comprising the steps of:

inserting an elongate member formed adjacent one or both of its proximal and distal ends with a fixture location, said elongate member being insertable substantially axially into the bone such that it spans the fracture; the fixture location being adapted to receive a fixing device inserted transversely of the elongate member and passing through part at least of the bone to be treated;

defining, by means of a jig temporarily affixed to the proximal end of the elongate member, the position of the fixture location and the line of insertion of the fixing device;

utilising said jig to pass a guide means through the fixture location and along said line of insertion;

anchoring said guide means into sound bone; and drilling, guided by the guide means, a bore communicating with the fixture location and adapted to accommodate the fixing device.

According to a still further aspect of the invention there is provided a method for the treatment of bone fracture, comprising the steps of:

forming adjacent at least the distal end of an elongate member, with a fixture location adapted to receive a fixing device inserted transversely of the elongate member and to engage with the aperture of the elongate member and inserting said elongate member substantially axially into the bone such that it spans the fracture; and utilising the fixing device in cooperation with the fixture location formed in the elongate member to draw the elongate member into intimate contact with said bone.

A particular application of the invention relates to the treatment of four-part and other fractures of the surgical neck and shaft of the humerus.

Comminuted four-part fractures of the upper end of the humerus present particular difficulties in imparting a sufficient degree of stability to the repaired bone structure. In attempting to stabilise the structure, it is necessary to take into account the forces acting on the fracture fragments, such as the supraspinatus muscle and the other muscles of the rotator cuff which act on the main proximal fragment of the fracture through the greater and lesser tuberosities. Sometimes, moreover, the greater tuberosity is a separate fragment and is displaced by muscular pull. The lesser tuberosity may also be a separate fragment, which tends to follow the greater tuberosity fragment because of the close attachment of the rotator cuff muscles.

Secure fixing of the distal end of an intramedullary nail enables the latter to be used as an internal plate, stabilising the repaired structure.

BRIEF DESCRIPTION OF THE DRAWINGS

In order that the invention may be clearly understood and readily carried into effect, one embodiment thereof will now be described, by way of example only, with reference to the accompanying drawings, of which:

FIG. 2 shows a side view of the patients fractured humerus a positioned prior to surgical procedure;

FIG. 3 shows a side view of a trocar positioned prior to reaming a channel for an intramedullary nail;

FIG. 4 shows a side view of the nail in position in the proximal humerus, with a jig removably attached to the nail;

FIG. 5 shows a side view similar to that of FIG. 4 and indicates the use of the jig to position the insertion of cannulate trocars into a cancellate region of the humeral head;

FIG. 6 shows a side view indicating the line of insertion of so-called K-wires axially of the trocars and into the subchondral bone of the humeral head;

FIG. 7 shows a side view similar to that shown in FIGS. 4 to 6 involving the use of centrally apertured drills inserted (following removal of the trocars) axially over the K-wires, using the latter as guides, to drill the lateral cortex to respectively receive proximal fixing screws;

FIG. 10 shows a side view indicating the line of insertion of K-wires axially of the trocars and into the cortical bone of the humeral shaft;

FIG. 11 shows a side view where at the distal end of the humeral shaft a cannulated drill is passed over a K-wire;

FIG. 12 shows a side view of insertion of a cannulated screw into the central position of the distal end of the nail.

FIG. 13 shows a side view of the humeral shaft where the proximal and distal screws have been inserted into the bone and through the intramedullary nail.

DETAILED DESCRIPTION OF THE PREFERRED EMBODIMENTS

Figure 1A:
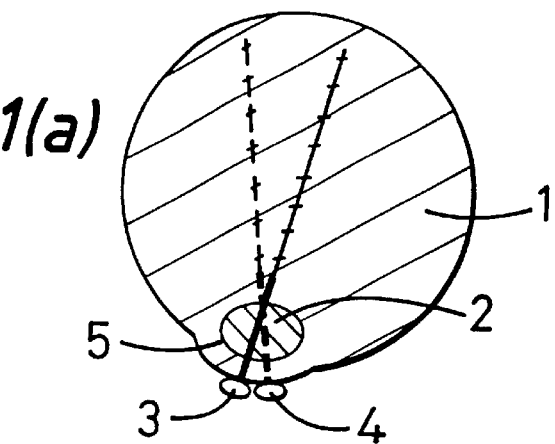
FIG. 1(a) shows a cross section of the proximal end of the patient's humerus from above with an elongate member 2 inserted axially throughout and 1(b) shows a similar view through the distal end of the humerus and elongate member 2.

Referring now to FIG. 1(a), the patient's humerus from above is shown at 1, with the proximal end of an elongate member, in this instance an intramedullary fixing nail, indicated at 2. First and second proximal fixing devices, in this case screws 3 and 4, are provided, as will be described more fully hereinafter. These screws pass, transversely of the nail 2, through respective holes in the shank thereof, into the sound bone of the humeral head, thereby creating a stable structure fixing the humeral head to the humeral shaft. It is preferable, though not essential, that the screws 3 and 4 are inserted through the nail 2 at different angles, though in substantially parallel planes, in order that they may engage portions of the humeral head that are relatively well separated from one another. This expedient assists in creating a structure stably fixing the humeral head to its shaft, though clearly the profile of the nail itself and the profile and/or dimensions of the respective holes therein through which the screws 3 and 4 pass must be formed so as to accommodate the splayed insertion of the screws.

Figure 1B:
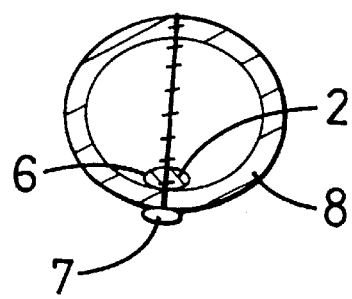
FIGS. 1(c) and 1(d) show respectively antero-posterior cross sectional and side views of the elongate member 2, with a plurality of holes therethrough.

Typically in this respect, the proximal portion 5 of the nail 2 is round or ovoid or rectangular in cross-section whereas the remainder of the nail 6 is ovoid or a curved oblong or rectangular, or otherwise conforms to a generally flattened cross-section, to enable it to be used as an internal plate, whereby, as shown in FIG. 1(b), the distal end of the nail may be drawn, by means of one or more lateral fixing screws 7, intimately against the internal surface of the humeral shaft 8.

Figure 1C:
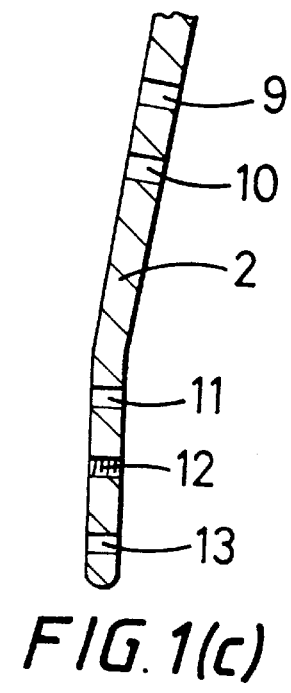
Figure 1D:
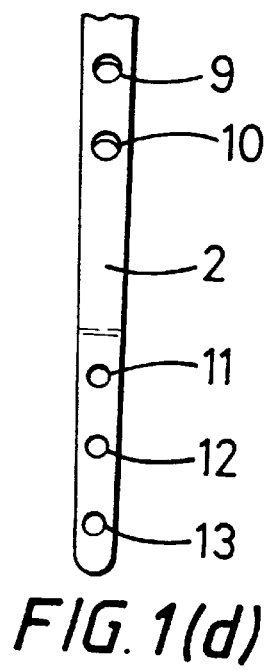
Figure 8:
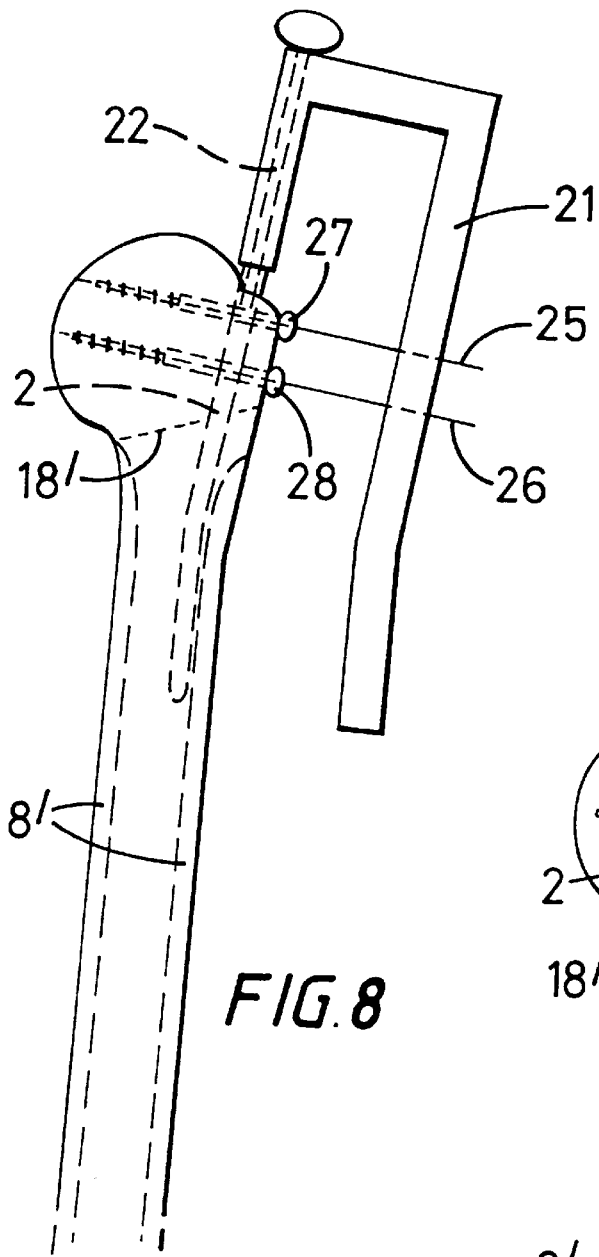
FIG. 8 shows a side view similar to that shown in FIGS. 4 to 7 and indicates the insertion of screws over the K-wires.
Figure 9:
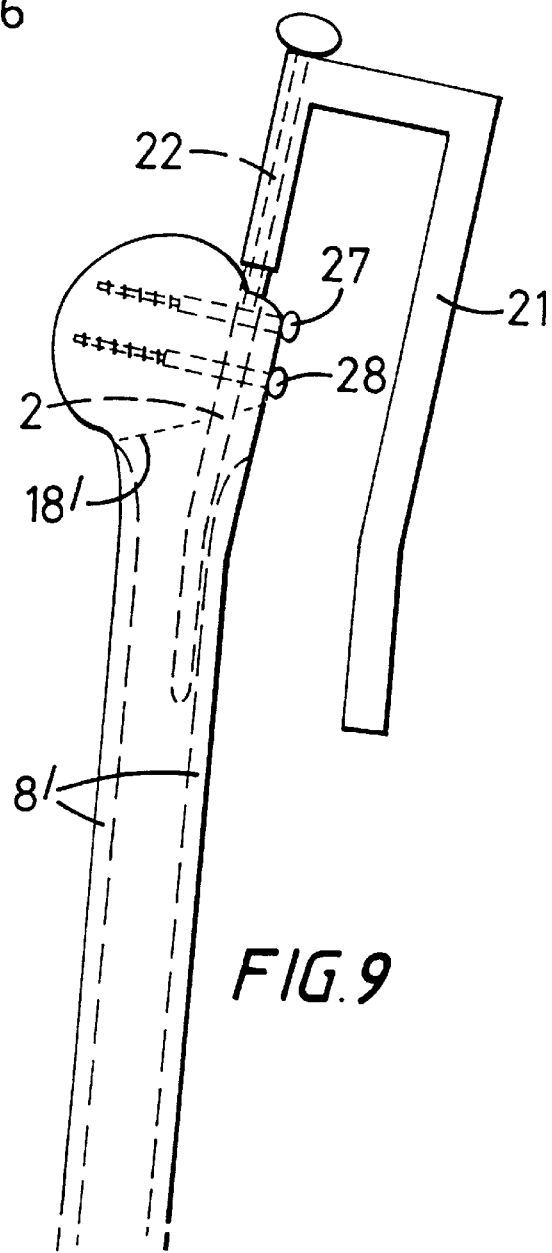
FIG. 9 shows a side view similar to that shown in FIG. 6 indicating the removal of K-wires from the humeral head.

FIGS. 1(c) and 1(d) show respectively antero-posterior cross sectional and side views of the nail 2, with a plurality of holes therethrough. Holes 9 and 10 are adjacent the proximal end of the nail and holes 11, 12 and 13 near the distal end thereof; at least the hole 12, but preferably all three being internally screw-threaded in order to permit the use of the nail 2 as a supportive plate, as illustrated in FIG. 1(b). The plates may contain any number of holes greater than 3 if necessary.

With reference now to FIG. 2, the humeral head and shaft are shown at 1 and 8 respectively, together with certain adjacent anatomical features such as the acromion process 14, the deltoid muscle 15, the greater tuberosity 16 and the glenoid 17. The surgical neck is indicated at 18 and the bone fracture is indicated at 18'.

The line of surgical approach is shown by arrow 19, splitting the deltoid muscle 15 to reach the point of insertion of the nail 2.

A trocar 20 is inserted, as shown in FIG. 3, close to the point at which the nail 2 is to be inserted, through a small incision just lateral to the acromion 14, so that it passes close to the lateral cortex. If this should prove difficult, for example because the humeral head is in abduction, the insertion of a bone awl or external fixator screw on an introducer into the humeral head (proximal fragment) will allow it to be manipulated into an appropriate position.

An antero-lateral approach to the shoulder may be used in addition, if the fracture proves difficult to reduce.

As shown in FIG. 4, a jig 21 is removably attached to the top of the nail 2 before introduction, to guide its insertion. The jig 21 is constructed and dimensioned so as to act as a guide for the insertion of transverse locking/location screws such as 3 and 4 at the proximal end and others at the distal end as previously outlined and as to be described in more detail hereinafter. Jig 21 engages a slot in the top of the nail 2 and is removably fixed in position by means of a screw 22 engaging an internal screw thread formed, in known manner, axially in the top end of the nail 2. The cortical bone of the humeral shaft in cross-section is represented at 8'.

In order to securely affix the proximal end of the nail 2 to the humeral head, the procedure illustrated in FIGS. 5 to 9 is followed. Using holes in the jig 21 designed to align with the holes 9 and 10 in the nail 2 (FIG. 1), for alignment, drill holes are made in the bone which ultimately define the positions of proximal screws in the cancellous bone of the humeral head. Trocars 23 and 24, with tissue protectors shown at 23a and 23b in FIG. 7, are first introduced through a small skin puncture. K-wires 25 and 26 are then passed axially down the trocars 23 and 24 and securely anchored into the subchrondal bone of the femoral head. A principal purpose of the wires is to serve as guides for a subsequently performed drilling procedure. The trocars are next removed and a drill which is axially apertured to accommodate a wire, inserted over each of the K-wires in turn (as indicated at 25a and 26a in FIG. 7) to drill into the lateral cortex in spaced-apart positions as described with reference to FIG. 1(a). Such a drill will hereinafter be referred to as a cannulated drill; the intention being that it is accurately guided by the K-wire passing centrally through it.

A measuring device is then used to measure the required screw length, and cannulated (axially apertured) cancellous screws 27 and 28 of length chosen to terminate 5 mm short of the subchondral bone of the humeral head are then passed over the K-wires, which later are then removed, leaving the screws 27 and 28 in position.

The screws to engage with the distal end of the nail 2 are inserted similarly, according to the sequence illustrated in FIGS. 10 to 13.

As at the proximal end of the nail 2, trocars 29, 30 and 31 with tissue protectors are inserted down to the bone, and respective K-wires 32, 33 and 34 passed therethrough to securely anchor in the opposite (medial) cortex through the respective holes 11, 12 and 13 (FIG. 1) in the nail 2. The middle hole of the three 12 is preferably drilled first, using a cannulated drill (indicated at 33a in FIG. 11) as before, guided by the K-wire 33 which passes axially through it. A cannulated screw 35, long enough to engage only the threaded hole 12 in the nail, is then inserted and screwed up, drawing the nail into intimate contact with the inner cortex so that it acts as an internal plate and thereby providing increased stability of the repair. The screw head should be large or preferably of normal size or with a washer large enough to spread the load to prevent the screw breaking out of what may be relatively osteoporatic bone in an elderly person. A second screw may be inserted in the same way to create even firmer contact between the nail 2 and the bone, and the other cannulated self-tapping screws 36, 37 are then likewise inserted, though these are of length sufficient to ensure gripping both of the respective screw threads formed in the holes 11 and 13 through the nail and of the medial cortex.

The jig 21 has then served its purpose and is removed; the axial screw-thread at the proximal end of the nail 2 thus vacated receiving instead a screw-in top 38 (FIG. 13) that holds a washer 39 which may be apertured (39a) and/or formed with radially extending claws (39b). The rotator cuff muscles may be stitched to the washer and/or attached to the nail via the aforesaid claws to transmit force through the nail 2 to the humeral shaft, creating a stable structure. Other fracture fragments may be attached by means of interfragmentary screws or circlage wires.

Figure 16:
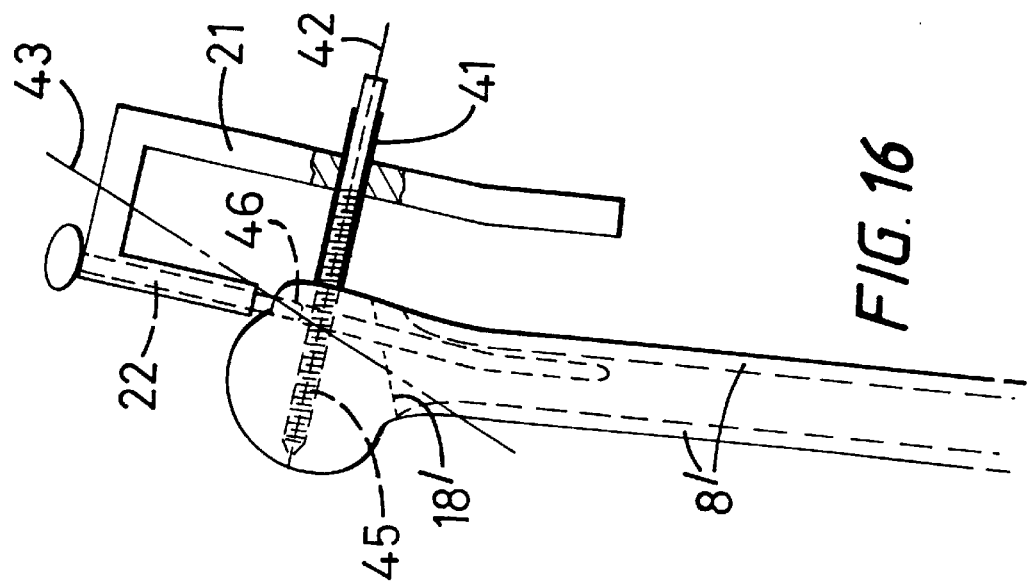
FIG. 16 shows the insertion of a drill bit along the guide wire, guided by the jig which is removably attached to a "short" nail.
Figure 19:
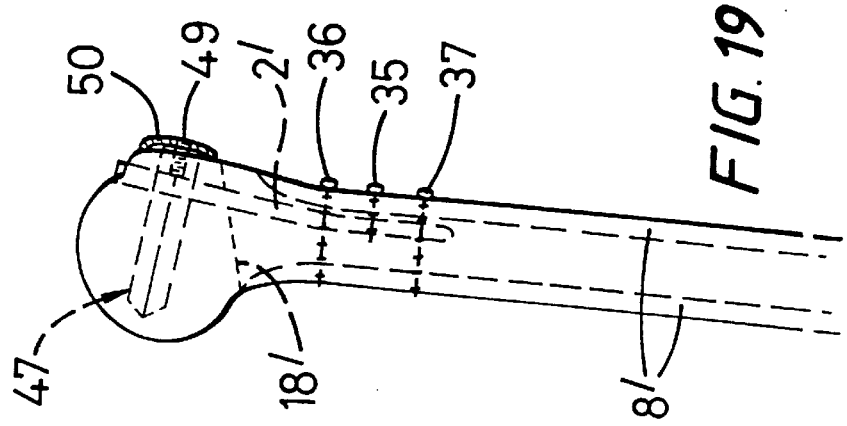
FIG. 19 shows a side view of the humeral shaft where the intramedullary nail has been inserted through the "flanged" bolt and secured at the distal end by screws. A locking grub screw is inserted into the "flanged" bolt and a toothed washer may also be inserted to stabilise Tuberosity fracture fragments.
Figure 18:
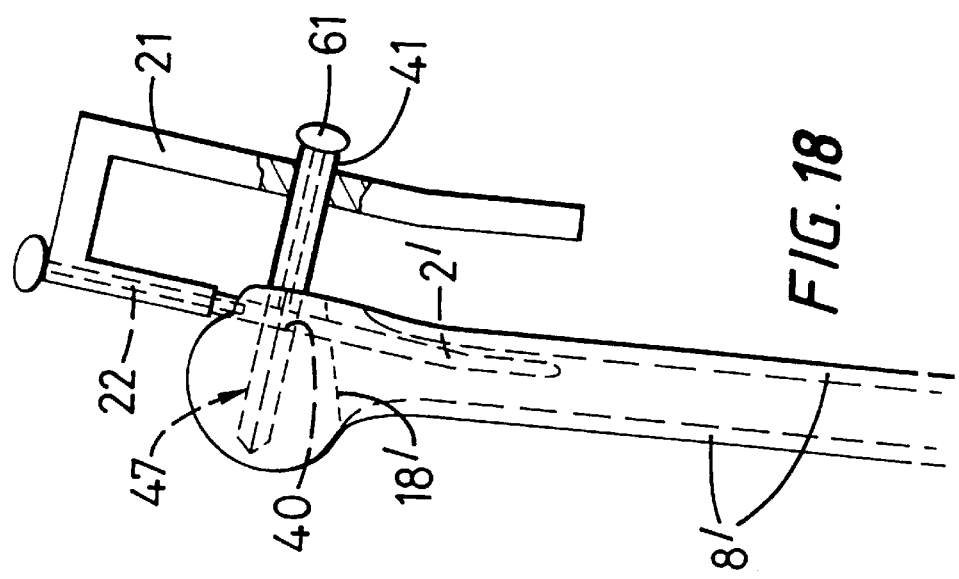
FIG. 18 shows insertion of an intramedullary nail through the aperture of the "flanged" bolt.
Figure 17:
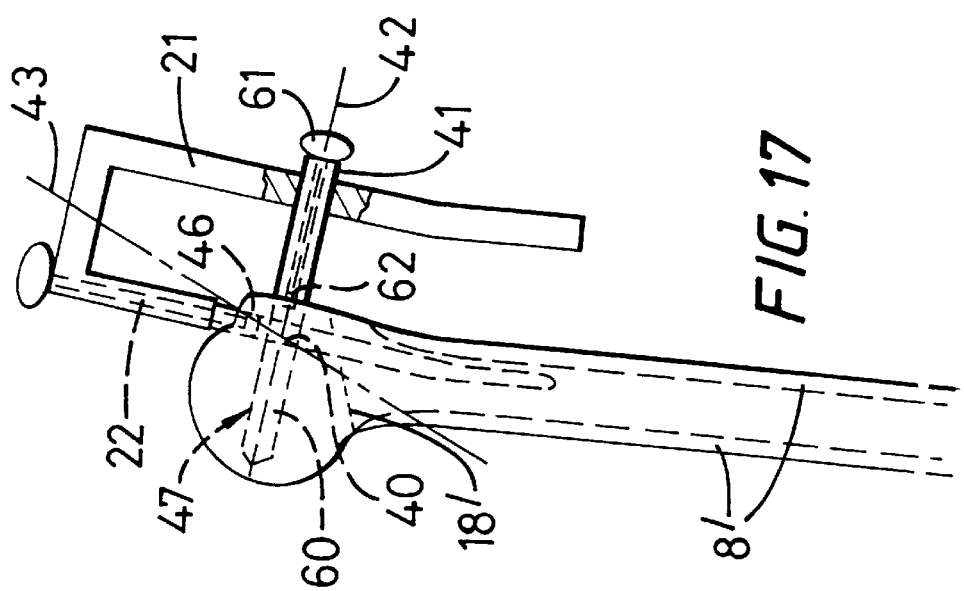
FIG. 17 shows a "flanged" bolt inserted along the guide wire.

In an alternative embodiment as shown in FIGS. 14–19, the insertion of two locking/location screws such as 3 and 4 may be substituted by the insertion of one "flanged" bolt 47 (FIGS. 17 to 19).

The steps previously demonstrated in FIGS. 5 to 9, may be substituted with the following. An intramedullary nail 2 is inserted into the humeral head whilst removably attached to a jig 21. A drill guide 41 is then used to aid the placement of a guide wire 42 through the humeral head 1 whereby the guide wire is passed axially down the drill guide and is securely anchored into the subchrondal bone of the humeral head (See FIG. 14). The jig allows accurate positioning of the guide wire. The preliminary intramedullary nail 2 is slotted into the coronal plane in such a manner as to permit its removal without displacing the affixed guide wire 42. The jig 21 contains a telescopic section to permit insertion and withdrawal of the nail 2.

Figure 15:
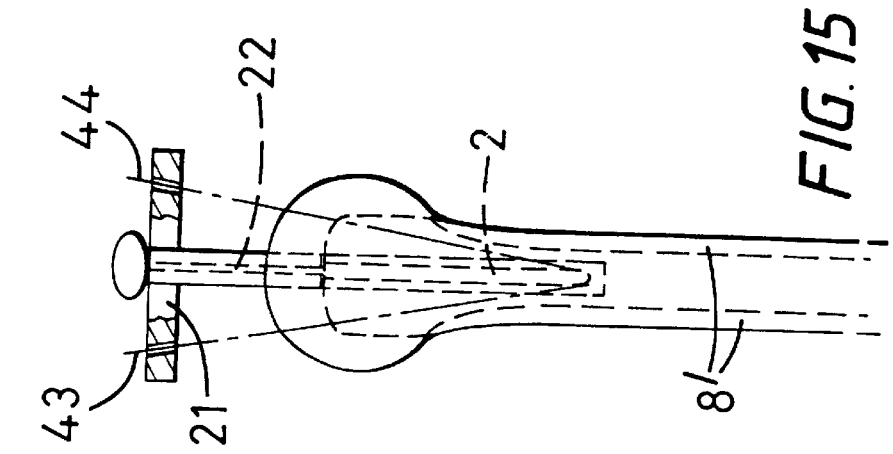
FIG. 15 shows a side view of the guide demonstrating the positioning of the K-wires.
Figure 14:
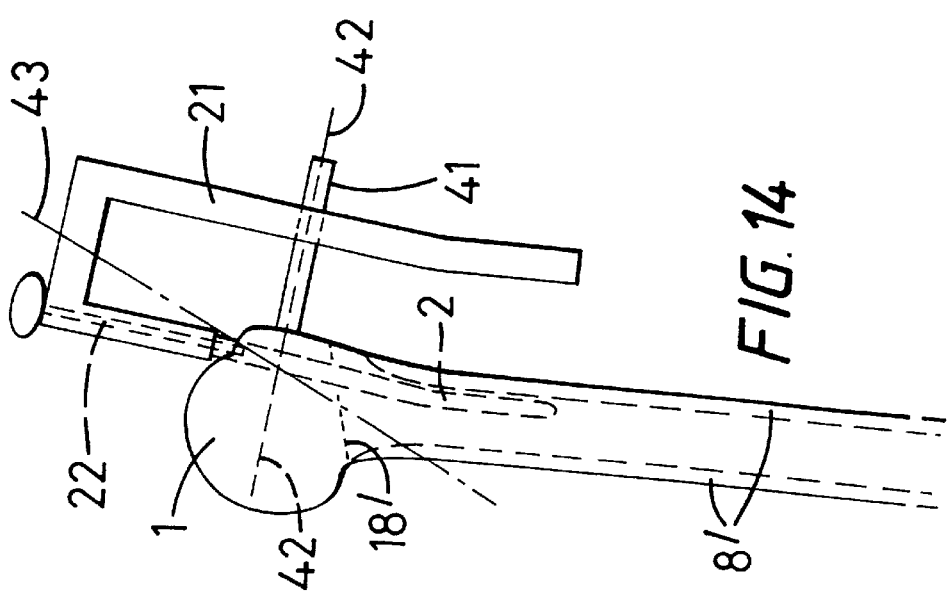
FIG. 14 shows a side view of the nail in position in the proximal humerus, with a jig removably attached to the nail to aid insertion of two K-wires and to aid insertion of a guide wire through a drill guide into the subchondral bone of the humeral head.

The jig 21 also aids accurate positioning of the two K-wires 43 and 44 (See FIG. 15). The function of the K-wires is to maintain the fracture position until a final nail 2' (See FIG. 18), which is to remain implanted in the bone (in the coronal plane) throughout treatment, is inserted into the bone.

Prior to insertion of the final nail 2', the preliminary intramedullary nail 2 is replaced by a "short" intermediate nail 46 as shown in FIG. 16. The "short" nail is inserted into the tuberosity in the coronal plane to provide additional stability to the K-wires whilst the humeral head is prepared for the "flanged" bolt 47.

A cannulated drill bit 45 is placed over the free end of the guide wire 42 (See FIG. 16) and is moved along the wire to drill into the bone. Once drilling is completed the drill bit 45 is removed and a cannulated "flanged" bolt 47 is inserted into the drilled hole along the guide wire 42 (See FIG. 17) running throughout the cannulated bolt. The "short" preliminary nail 46 is still in place and continues to provide stability while the "flanged" bolt is being inserted. The "flanged" bolt 47 comprises an insertion section 60 and an extension section 61. The extension section 61 is removably attached to the insertion section by way of a threaded locking pin 62.

Once the "flanged" bolt has been inserted, the "short" intermediate nail 46 is removed and the final intramedullary nail 2' inserted through an aperture 40 provided in the "flanged" bolt 47. The guide wire 42 and K-wires 43 and 44 can then be removed (See FIG. 18).

When the final intramedullary nail 2' has been safely located in position through the bolt 47, the bolt extension 61 and jig 21 can be removed. The final nail 2' and bolt 47 are locked together by insertion of a grub screw 49 which thereby stabilizes the structure, locking the final nail 2' (See FIG. 19). A toothed washer 50 may be inserted to enhance stability of tuberosity fracture fragments. Screws such as 35, 36 and 37 are inserted as before (See FIGS. 10 to 13) in the distal portion of the final nail 2' to secure the implant to the distal fracture fragments.

It will be appreciated by those skilled in the art that relatively longer nails can be used to provide fixation of fractures of the shaft of the bone. It will also be appreciated that such a nail can be adapted for use in any bone throughout the body.

What is claimed is:

1. Apparatus for the treatment of a fracture in a bone, the apparatus comprising:

first and second fixing devices, the first fixing device having a shorter length than the second fixing device; and an elongate member capable of substantially axial insertion into the bone to span the fracture, the elongate member having adjacent at least the distal end thereof a first fixture location means for engagement with the first fixing device inserted through the bone transversely of the elongate member, and the elongate member having a second fixture location means for engagement with the second fixing device inserted through the bone transversely of the elongate member;

wherein the first fixture location means and a distal end of the first fixing device are formed to secure together whereby during securing the first fixture location means and the proximal end of the first fixing device are drawn together with the proximal end of the first fixing device contacting the outer surface of the bone and the elongate member being drawn against the inner surface of the bone.

2. Apparatus according to claim 1 wherein said first fixture location means comprises a threaded aperture and the first fixing device comprises a screw having a corresponding threaded portion.

3. Apparatus according to claim 2 wherein said screw has a length limited to engagement with said fixture location means.

4. Apparatus according to claim 2 wherein the second fixture location means comprises at least one further aperture provided in the distal end of said elongate member for receiving a respective screw.

5. Apparatus according to claim 4 wherein at least one said further aperture comprises a threaded aperture.

6. Apparatus according to claim 1 wherein the elongate member is in the form of an intramedullary nail having the region of the distal end configured to permit close conformity to the surface of the bone.

7. Apparatus according to claim 1 further comprising one or more additional fixing devices; wherein the proximal end of said elongate member is formed with one or more apertures to accommodate transversely disposed respective additional fixing devices.

8. Apparatus according to claim 7 wherein a plurality of apertures are formed in the proximal end of the elongate member with an orientation whereby respective transversely disposed additional fixing devices are accommodated by passing through the respective apertures into sound bone in substantially parallel planes transverse to said elongate member, but axially misaligned so as to respectively engage areas of bone more widely separated than the areas that would have been engaged by the additional fixing devices had the apertures been oriented in axial alignment with one another.

9. Apparatus according to claim 1 wherein the second fixing device has an aperture therein; and wherein the elongate member is formed for insertion through the second fixing device aperture whereby the proximal end of said elongate member is fixed by contact with the second fixing device.

10. Apparatus as claimed in claim 1, including a jig temporarily affixable to the proximal end of the elongate member to define the line of insertion of the fixing device relative to the fixture location means; further including a guide means adapted to pass through the fixture location means to act as a guide for the desired location of the fixing device; and wherein the guide means is adapted to accommodate the fixing device.

11. Apparatus according to claim 10, wherein the guide means comprises a guide wire and the fixing device is axially apertured to accommodate the guide wire.

12. A method of treating a fracture in a bone, comprising the steps of:

inserting an elongate member substantially axially into the bone to span the fracture, the elongate member having adjacent at least the distal end thereof a fixture location means;

inserting a fixing device through the bone; and engaging the fixing device with the fixture location means to draw the elongate member into intimate contact with the inner surface of the bone.

13. A method as claimed in claim 12, wherein more than one fixing device is provided and each fixing device engages a respective aperture in the distal end of the elongate member.

14. A method as claimed in claim 12, wherein at least one additional fixing device is engaged with at least one respective aperture at the proximal end of the elongate member.

15. A method as claimed in claim 14, wherein more than one additional fixing device is provided and the additional fixing devices are engaged with the elongate member and the bone in substantially parallel planes but axially misaligned so as to engage areas of bone more widely separated than the areas that would have been engaged by the additional fixing devices had they been orientated in axial alignment with one another.

16. A method as claimed in claim 14, wherein the elongate member is passed through an aperture in the at least one additional fixing device.

17. A method as claimed in claim 12, including the steps of:

affixing a jig to the proximal end of the elongate member, the jig defining the line of insertion of the fixing device relative to the position of the fixture location means;

using the jig to pass a guide means through the fixture location means along the line of insertion to act as a guide for the desired location of the fixing device;

anchoring the guide means into sound bone; and drilling a bore in the bone in communication with the fixture location means, the path of the drill being guided by the guide means.

18. A method as claimed in claim 17, wherein the guide means comprises a wire and the bore is drilled by inserting an axially apertured drill over the wire.

19. A method as claimed in claim 17, wherein the fixing device comprises an axially apertured screw, the screw being inserted into the bone over the wire.

* * * * *